(12) United States Patent
Pipke

(10) Patent No.: US 10,722,179 B2
(45) Date of Patent: *Jul. 28, 2020

(54) RESIDUAL-BASED MONITORING OF HUMAN HEALTH

(71) Applicant: PhysIQ, Inc., Naperville, IL (US)

(72) Inventor: Robert Matthew Pipke, Oak Park, IL (US)

(73) Assignee: PhysIQ, Inc., Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/658,732

(22) Filed: Jul. 25, 2017

(65) Prior Publication Data
US 2017/0319145 A1 Nov. 9, 2017

Related U.S. Application Data

(63) Continuation of application No. 14/310,867, filed on Jun. 20, 2014, now Pat. No. 9,743,888, which is a (Continued)

(51) Int. Cl.
*A61B 5/00* (2006.01)
*A61B 5/0205* (2006.01)
(Continued)

(52) U.S. Cl.
CPC .......... *A61B 5/7264* (2013.01); *A61B 5/0205* (2013.01); *A61B 5/0402* (2013.01); *A61B 5/14551* (2013.01); *G06F 9/545* (2013.01); *G06K 9/6215* (2013.01); *G16H 50/20* (2018.01); *G16H 50/50* (2018.01); *G16H 50/70* (2018.01);
(Continued)

(58) Field of Classification Search
CPC combination set(s) only.
See application file for complete search history.

(56) References Cited

U.S. PATENT DOCUMENTS 4,937,763 A 6/1990 Mott
5,113,483 A 5/1992 Keeler
(Continued)

FOREIGN PATENT DOCUMENTS

WO 2000067412 11/2000

OTHER PUBLICATIONS

Baxi, Amit, and Kodalapura, Nagaraju, A Self-Managing Framework for Health Monitoring, reprinted from Intel® Technology Journal, Nov. 9, 2006, vol. 10, Issue 4, pp. 312-327.
(Continued)

*Primary Examiner* — Michael W Kahelin
*Assistant Examiner* — Shirley X Jian
(74) *Attorney, Agent, or Firm* — Fitch, Even, Tabin & Flannery LLP

(57) ABSTRACT

Improved human health monitoring is provided in the context of sensor measurements of typical vital signs and other biological parameters, by a system and method using an empirical model of the parameters and disposed to estimate values of the parameters in response to actual measurements. Residuals resulting from the difference between the estimates and actual measurements are analyzed for robust indications of incipient health issues. Residual analysis is both more robust and more sensitive than conventional univariate range checking on vital signs.

13 Claims, 3 Drawing Sheets

Related U.S. Application Data continuation of application No. 11/564,679, filed on Nov. 29, 2006, now Pat. No. 8,795,170.

(60) Provisional application No. 60/740,423, filed on Nov. 29, 2005.

(51) Int. Cl.

| | | |
|---|---|---|
| *G06K 9/62* | (2006.01) | |
| *G16H 50/70* | (2018.01) | |
| *G16H 50/20* | (2018.01) | |
| *G16H 50/50* | (2018.01) | |
| *G06F 9/54* | (2006.01) | |
| *A61B 5/0402* | (2006.01) | |
| *A61B 5/1455* | (2006.01) | |
| *G16B 5/00* | (2019.01) | |
| *G16B 99/00* | (2019.01) | |
| *A61B 5/021* | (2006.01) | |
| *A61B 5/0245* | (2006.01) | |
| *A61B 5/0456* | (2006.01) | |
| *A61B 5/08* | (2006.01) | |
| *A61B 5/11* | (2006.01) | |
| *A61B 5/145* | (2006.01) | |
| *G16H 50/30* | (2018.01) | |

(52) U.S. Cl.
CPC .......... *A61B 5/021* (2013.01); *A61B 5/02055* (2013.01); *A61B 5/02455* (2013.01); *A61B 5/0456* (2013.01); *A61B 5/0816* (2013.01); *A61B 5/11* (2013.01); *A61B 5/145* (2013.01); *A61B 5/14532* (2013.01); *A61B 5/7267* (2013.01); *G16B 5/00* (2019.02); *G16B 99/00* (2019.02); *G16H 50/30* (2018.01)

(56) References Cited

U.S. PATENT DOCUMENTS

| | | | |
|---|---|---|---|
| 5,402,521 A | 3/1995 | Niida | |
| 5,463,768 A | 10/1995 | Cuddihy | |
| 5,465,321 A | 11/1995 | Smyth | |
| 5,479,574 A | 12/1995 | Glier | |
| 5,481,647 A | 1/1996 | Brody | |
| 5,495,168 A | 2/1996 | De Vries | |
| 5,526,446 A | 6/1996 | Adelson | |
| 5,539,638 A | 7/1996 | Keeler | |
| 5,574,387 A | 11/1996 | Petsche | |
| 5,640,103 A | 6/1997 | Petsche | |
| 5,668,944 A | 9/1997 | Berry | |
| 5,682,317 A | 10/1997 | Keeler | |
| 5,745,382 A | 4/1998 | Vilim | |
| 5,764,509 A | 6/1998 | Gross | |
| 5,774,379 A | 6/1998 | Gross | |
| 5,792,072 A | 8/1998 | Keefe | |
| 5,819,291 A | 10/1998 | Haimowitz | |
| 5,933,818 A | 8/1999 | Kasravi | |
| 5,987,399 A | 11/1999 | Wegerich | |
| 6,090,044 A | 7/2000 | Bishop | |
| 6,108,616 A | 8/2000 | Borchers | |
| 6,110,214 A | 8/2000 | Klimasauskas | |
| 6,119,111 A | 9/2000 | Gross | |
| 6,181,975 B1 | 1/2001 | Gross | |
| 6,202,038 B1 | 3/2001 | Wegerich | |
| 6,240,372 B1 | 5/2001 | Gross | |
| 6,245,517 B1 | 6/2001 | Chen | |
| 6,246,972 B1 | 6/2001 | Klimasauskas | |
| 6,278,962 B1 | 8/2001 | Klimasauskas | |
| 6,289,330 B1 | 9/2001 | Jannarone | |
| 6,458,080 B1 | 10/2002 | Brown | |
| 6,524,239 B1 | 2/2003 | Reed | |
| 6,551,252 B2 | 4/2003 | Sackner | |
| 6,553,334 B2 | 4/2003 | Gross | |
| 6,556,939 B1 | 4/2003 | Wegerich | |
| 6,567,752 B2 | 5/2003 | Cusumano | |
| 6,572,545 B2 | 6/2003 | Knobbe | |
| 6,602,191 B2 | 8/2003 | Quy | |
| 6,609,036 B1 | 8/2003 | Bickford | |
| 6,616,613 B1 | 9/2003 | Goodman | |
| 6,625,569 B2 | 9/2003 | James | |
| 6,678,639 B2 | 1/2004 | Little | |
| 6,687,654 B2 | 2/2004 | Smith, Jr. | |
| 6,775,641 B2 | 8/2004 | Wegerich | |
| 6,804,628 B2 | 10/2004 | Gross | |
| 6,804,656 B1 | 10/2004 | Rosenfeld | |
| 6,826,552 B1 | 11/2004 | Grosser | |
| 6,834,203 B2 | 12/2004 | Bardy | |
| 6,853,920 B2 | 2/2005 | Hsiung | |
| 6,876,943 B2 | 4/2005 | Wegerich | |
| 6,892,163 B1 | 5/2005 | Herzog | |
| 6,898,469 B2 | 5/2005 | Bickford | |
| 6,917,839 B2 | 7/2005 | Bickford | |
| 6,925,324 B2 | 8/2005 | Shusterman | |
| 6,951,539 B2 | 10/2005 | Bardy | |
| 6,952,662 B2 | 10/2005 | Wegerich | |
| 6,957,172 B2 | 10/2005 | Wegerich | |
| 6,975,962 B2 | 12/2005 | Wegerich | |
| 6,999,899 B2 | 2/2006 | Gross | |
| 7,027,953 B2 | 4/2006 | Klein | |
| 7,085,675 B2 | 8/2006 | Wegerich | |
| 7,174,205 B2 | 2/2007 | Moreno | |
| 7,308,385 B2 | 12/2007 | Wegerich | |
| 7,373,283 B2* | 5/2008 | Herzog | G06F 17/18 703/2 |
| 7,398,115 B2 | 7/2008 | Lynn | |
| 7,403,869 B2 | 7/2008 | Wegerich | |
| 7,409,320 B2 | 8/2008 | Wegerich | |
| 7,502,643 B2* | 3/2009 | Farringdon | A61B 5/0428 600/509 |
| 7,539,597 B2* | 5/2009 | Wegerich | G05B 23/0254 700/108 |
| 7,565,262 B2 | 7/2009 | Yuan | |
| 7,634,360 B2 | 12/2009 | Davalos | |
| 7,640,145 B2 | 12/2009 | Wegerich | |
| 7,670,295 B2 | 3/2010 | Sackner | |
| 7,674,231 B2 | 3/2010 | McCombie | |
| 7,818,131 B2 | 10/2010 | Mott | |
| 7,844,558 B2 | 11/2010 | Yuan | |
| 8,275,577 B2* | 9/2012 | Herzog | F22B 37/10 702/183 |
| 8,290,129 B2 | 10/2012 | Rogers | |
| 8,311,774 B2 | 11/2012 | Hines | |
| 8,478,542 B2 | 7/2013 | Mott | |
| 8,515,680 B2* | 8/2013 | Pipke | G06F 19/24 435/6.1 |
| 8,597,185 B2* | 12/2013 | Pipke | A61B 5/0205 600/301 |
| 8,620,591 B2* | 12/2013 | Wegerich | A61B 5/0205 600/301 |
| 8,620,853 B2* | 12/2013 | Herzog | G06K 9/6215 706/52 |
| 8,660,980 B2* | 2/2014 | Herzog | G05B 23/0254 706/52 |
| 8,795,170 B2* | 8/2014 | Pipke | A61B 5/0205 600/301 |
| 9,250,625 B2* | 2/2016 | Herzog | G05B 23/0243 |
| 9,256,224 B2* | 2/2016 | Herzog | G05B 23/0283 |
| 9,743,888 B2* | 8/2017 | Pipke | A61B 5/0205 |
| 2002/0040278 A1 | 4/2002 | Anuzis | |
| 2002/0152056 A1* | 10/2002 | Herzog | G06F 17/18 703/2 |
| 2002/0183971 A1* | 12/2002 | Wegerich | G05B 23/0254 702/185 |
| 2003/0060808 A1 | 3/2003 | Wilk | |
| 2003/0109951 A1 | 6/2003 | Hsiung | |
| 2003/0126258 A1 | 7/2003 | Conkright | |
| 2003/0144829 A1 | 7/2003 | Geatz | |
| 2004/0034295 A1 | 2/2004 | Salganicoff | |
| 2004/0122702 A1 | 6/2004 | Sabol | |
| 2004/0193064 A1 | 9/2004 | Shusterman | |
| 2004/0199482 A1 | 10/2004 | Wilson | |
| 2004/0236188 A1 | 11/2004 | Hutchinson | |

(56) References Cited

U.S. PATENT DOCUMENTS

| | | | |
|---|---|---|---|
| 2004/0243636 A1 | 12/2004 | Hasiewicz | |
| 2005/0021212 A1 | 1/2005 | Gayme | |
| 2005/0027205 A1 | 2/2005 | Tarassenko | |
| 2005/0113650 A1 | 5/2005 | Pacione | |
| 2005/0113703 A1* | 5/2005 | Farringdon | A61B 5/0428 600/509 |
| 2005/0130230 A1 | 6/2005 | Davalos | |
| 2005/0222508 A1 | 10/2005 | Moreno | |
| 2005/0228591 A1 | 10/2005 | Hur | |
| 2005/0261837 A1* | 11/2005 | Wegerich | G06N 5/025 702/19 |
| 2006/0111644 A1* | 5/2006 | Guttag | A61B 5/048 600/544 |
| 2006/0271407 A1 | 11/2006 | Rosenfeld | |
| 2006/0293859 A1* | 12/2006 | Pipke | G06F 19/24 702/19 |
| 2007/0010720 A1* | 1/2007 | Mott | G16H 50/70 600/300 |
| 2007/0282212 A1 | 12/2007 | Sierra | |
| 2008/0071501 A1* | 3/2008 | Herzog | F22B 37/10 702/185 |
| 2008/0183425 A1 | 7/2008 | Hines | |
| 2011/0093244 A1* | 4/2011 | Pipke | G06F 19/24 703/2 |
| 2011/0172504 A1* | 7/2011 | Wegerich | A61B 5/0205 600/301 |
| 2014/0107433 A1* | 4/2014 | Wegerich | A61B 5/0205 600/301 |

OTHER PUBLICATIONS

Coiera, Enrico W., Monitoring diseases with empirical and model generated histories, revised version of a paper that originally appeared in Artificial Intelligence in Medicine, 1990, No. 2, pp. 135-147.

Dawant, Benoit M., Uckun, Serdar, Lindstrom, Daniel P., and Manders, Eric J., Model-Based Signal Analysis and Interpretation in the Intensive Care Unit, IEEE Engineering in Medicine and Biology Society, vol. 3, Oct./Nov. 1992, pp. 87 4-875.

Diaz, Ignacio, and Hollmen, Jaakko, Residual Generation and Visualization for Understanding Novel Process Conditions, Engineering Applications of Artificial Intelligence, Sep. 2007, pp. 757-765, vol. 20, Issue 6, Pergamon Press, Inc., Tarrytown, New York.

Doyle, Jon, Kohane, Isaac, Long, William, and Szolovits, Peter, The Architecture of MAITA: A Tool for Monitoring, Analysis, and Interpretation, MIT Computer Science and Artificial Intelligence Laboratory, Technical Report No. 951, May 2004, pp. 1-67.

Embrechts, Mark J., Boleslaw Szymanski, and Karsten Sternickel. "Introduction to scientific data mining: Direct kernel methods and applications." Computationally Intelligent Hybrid Systems: The Fusion of Soft and Hard Computing (2004): 317-362. http://www.cs.rpi.edu/~szymansk/papers/ieee-book.04.pdf accessed on Jun. 20, 2016.

Gribok, Andrei, McKenna, Thomas, and Reifman, Jaques, Regularization of Body Core Temperature Prediction During Physical Activity, Proceedings of the 28th IEEE EMBS Annual International Conference, New York City, New York, Aug. 30-Sep. 3, 2006, pp. 459-463.

Griebenow, R.D., P.E., Hansen, E.J., Sudduth, A.L, P.E., Applied Pattern Recognition for Plant Monitoring and Data Validation, presented at the Fifth International Joint ISA POWID/EPRI Controls and Instrumentation Conference, La Jolla, California, Jun. 19-21, 1995, pp. 11.

Hansson, Anders, and Miksch, Silvia, On-Line Identification of a Patient-Disease Model for Mechanical Ventilation, Intelligent Data Analysis in Medicine and Pharmacology, 15th International Joint Conference on Artificial Intelligence IJCAI-97, Nagoya, Japan, Aug. 23-29, 1997.

Hau, David T., and Coiera, Enrico W., Learning Qualitative Models of Dynamic Systems, Machine Learning, 1993, pp. 177-211, vol. 26, Kluwer Academic Publishers, Boston.

International Application No. PCT/US2006/045656, International Search Report, dated Apr. 27, 2017, 1 page.

Jung, Insung, Park, Seung Chan, Wang, Gi-Nam, Two phase reverse neural network based human vital sign prediction system, presented at CIMCA-IAWTIC, Nov. 28-Dec. 1, 2006, pp. 135, Sydney, Australia.

Magoulas, George D., and Prentza, Andriana, Machine Learning in Medical Applications, Lecture Notes in Computer Science, 2001, pp. 300-307, vol. 2049, Springer Berlin, Heidelberg.

Manders, Eric J., Msee, Dawant, Benoit M., Ph.D., Data Acquisition for an Intelligent Bedside Monitoring System, Conference of the IEEE Engineering in Medicine and Biology Society, No. 7.2.1: Monitoring in Critical Care, 1996, pp. 1987-1988, Amsterdam.

Meyer, Claudia M., Maul, William A., and Dhawan, Atam P., SSME Parameter Estimation and Model Validity Using Radial Basis Function Neural Networks, presented at conference on Advanced Earth to Orbit Propulsion Technology, 1994, pp. 11.

Norris, Patrick R., Dawant, Benoit M., Ph.D., and Suwanmongkol, Improving the Simon Architecture for Critical Case Intelligent Monitoring, Proc AMIA Symp. 1998, pp. 1048.

Norris, Patrick R., Suwanmongkol, Karlkim, Geissbuhler, Antoine, and Dawant, Benoit M., The Simon Architecture: Distributing Data, Tasks, and Knowledge in Intelligent ICU Monitoring Systems, Computers in Anaesthesia and Intensive Care: Knowledge-Based Information Management, Aalborg, Denmark, Jun. 20, 1999.

Savell, C. Thomas, Borsotto, Maurizio, Reifman, Jaques, and Hoyt, Reed W., Life Sign Decision Support Algorithms, Studies in Health Technology and Informatics, 2004, pp. 1453-1457, vol. 207, Issue Part 2, Netherlands.

Singer, Ralph M., Gross, Kenny C., King, Ronald W., and Wegerich, Stephan W., A Pattern-Recognition-Based, Fault-Tolerant Monitoring and Diagnostic Technique, Proceeding of Symposium on Nuclear Reactor Surveillance and Diagnostics (SMORN VII), Jun. 19-23, 1995, pp. 13-21, vol. 2, Arignon, France.

Steimann, Friedrich, Dissertation: Diagnostic Monitoring of Clinical Time Series, Technical University of Vienna, 1995, pp. 1-138, Vienna, Austria (first three pages in German, English thereafter).

Tarassenko, L., Hann, A., and Young, D., Integrated monitoring and analysis for early warning of patient deterioration, British Journal of Anaesthesia, Jul. 2006, pp. 64-68, vol. 97, No. 1, Oxford University Press.

Tarassenko, L., Hann, A., Patterson, A., Braithwaite, E., Davidson, K., Barber, V., and Young, D., Biosign #: Multi-Parameter Monitoring for Early Warning of Patient Deterioration, presented at The 3rd IEE International Seminar on Medical Applications of Signal Processing, Nov. 3-4, 2005, pp. 71-76.

Tsien, Christine L., Trendfinder: Automated Detection of Alarmable Trends, Massachusetts Institute of Technology, Jun. 2000, pp. 1-241.

Uckun, S., Lindstrom, D.P., Manders, E.J., Dawant, B.M., Using Models of Physiology for Intelligent Patient Monitoring, Conference of the IEEE Engineering in Medicine and Biology Society, 1991, pp. 1308-1309, vol. 13, No. 3.

Uckun, Serdar, MD, PhD., Intelligent Systems in Patient Monitoring and Therapy Management: A Survey of Research Projects, International Journal of Clinical Monitoring and Computing, Nov. 1994, pp. 241-253, vol. 11, No. 4, Springer Netherlands.

Wegerich, S., Xu, X., A Performance Comparison of Similarity-Based and Kernel Modeling Techniques, Proceedings of the Maintenance and Reliability Conference, MARCON 2003, Knoxville, Tennessee, May 4-7, 2003.

Wegerich, Stephan W., Similarity Based Modeling of Time Synchronous Averaged Vibration Signals for Machinery Health Monitoring, Proceedings of the IEEE Aerospace Conference, 2004, pp. 3654-3662, Vol. 6.

Wegerich, Stephan W., Wilks, AI D., and Pipke, Robert M., Nonparametric Modeling of Vibration Signal Features for Equipment Health Monitoring, Proceedings of the IEEE Aerospace Conference, 2003, pp. 3113-3121, vol. 7, Big Sky, Montana.

* cited by examiner

RESIDUAL-BASED MONITORING OF HUMAN HEALTH

CROSS REFERENCE TO RELATED APPLICATIONS

This application is a continuation of prior U.S. patent application Ser. No. 14/310,867, filed Jun. 20, 2014, which is a continuation of U.S. patent application Ser. No. 11/564,679, filed Nov. 29, 2006, now U.S. Pat. No. 8,795,170, which claims the benefit of priority under 35 U.S.C. § 119(e) to U.S. Provisional application No. 60/740,423 filed Nov. 29, 2005.

BACKGROUND OF THE INVENTION

1. Field of the Invention

The present invention relates generally to the field of human health monitoring, and more particularly to the use of multivariate models for analysis of measurements of biological parameters to provide residual-based assessment of human health indicators.

2. Brief Description of the Related Art

Detection and diagnosis of disease conditions in humans is critically important to maintaining health of individuals and aiding in the recuperation of patients. While early and aggressive detection are highly desirable, this must be balanced with the health care delivery costs of false alerts and misdiagnoses. Accurate and actionable detection of unfolding health issues, whether in a time-critical setting such as an intensive care unit (ICU) or in longer-term health monitoring such as home monitoring of chronically ill people or performance monitoring of athletes for example, is a problem that has been the focus of much medical attention. Current demographic trends indicate that as people live longer, they have an increasing number of chronic health issues to deal with. In addition, some diseases that previously had high mortality are becoming manageable long-term chronic conditions. Consequently, an increasing number of people require ongoing monitoring, heavily taxing the healthcare delivery system.

According to conventional medical practice, human health monitoring in a critical care environment is typically practiced by means of a variety of real-time sensor measurements such as electrocardiogram (ECG), pulse oximetry, respiration and blood pressure, as well as laboratory tests of the blood, urine, and other bodily fluids. Longer term monitoring may include these variables, as well as weight measurement, medication dosing measurements and other qualitative assessments of condition. These measurements are typically compared in a univariate manner to prescribed normal ranges known for the (healthy) population generally, and indications of disease or developing conditions of poor health are diagnosed from these measurements vis-à-vis the standard ranges. Combined with qualitative observation by medically trained personnel, this forms the baseline practice in medicine in the monitoring of patients and healthy individuals for purposes of detecting ill health conditions and disease, and is a staff-intensive approach to the delivery of healthcare.

It has long been a goal of medical care to provide automated reliable monitoring of patients using sensors and computer technology. More recently, with the improved availability of digital instrumentation, and research into computer systems that embody the expertise of medical personnel, systems have been made available that provide for rules-based monitoring of patients based on vital signs and laboratory test results. Such systems are used in hospital settings to provide an auxiliary support system for monitoring patients in, e.g., an ICU. An expert rules execution engine can be programmed to combine threshold detection triggers across a variety of signals to diagnose or rule out a condition that requires human medical staff intervention.

These systems have met with limited success. The expert rules are difficult to design in a way that can be effectively generalized across the human population, and across the variety of states the patients present with. What may be accurate for a young trauma patient in recovery may be subject to false alerts and detection inaccuracies when applied to an elderly cardiology patient.

In another approach of the prior art, artificial intelligence techniques arguably more akin to the data fusion capabilities of the human expert, such as neural networks, have been applied to data from human patient monitoring in an attempt to provide better automated monitoring and diagnostics. A neural network is trained from a set of examples to learn certain associations and patterns. For example, a set of patient data associated with a disease state and another set of patient data associated with a healthy state are used to train the neural network to recognize the disease state and diagnose it. Typically, it has been known to input a set of patient data to a trained neural network and obtain a classification as output, either as a determination of health versus illness, or as a diagnosis of a particular condition. An alternative approach also known in the art is to input a set of patient data to a neural network and obtain a scalar rating value as output, e.g., degree of illness or progression of disease. However, the manner in which the neural network output was generated based on the input data and the training data is obscured to an observer because of the nonlinear nature of neural computing. Furthermore, it is difficult to design such a "black box" approach in a way that generalizes well beyond the training data. As a result, these approaches have met with wide variation in success, which ultimately undermines their reliability.

A major problem for all these prior art approaches is the dynamic nature of biological systems. Humans represent a biological system with a complex internal control and feedback system responsive to conditions and demands on the body for regulating critical aspects of health such as blood pressure, blood chemistry, oxygenation and the like. The measurements typically made to monitor health are subject to wide variation depending on activity state, age, weight, nutrition and disease state. As a consequence, it is difficult to assign proper trigger levels to thresholds for monitored variables and so these tend to be set on a demographic basis at levels that can only indicate critical and immediate health problems. For example, pulse rate monitoring may be set such that only extremely high or extremely low (or zero) pulse rates trigger an alarm. Even in more advanced prior art solutions combining variables and thresholds into multivariate rules, it remains extremely difficult to design rules that provide actionable lead time notice of a genuine developing problem while maintaining a low false alert rate. Similarly, neural networks for classification have been confounded with regard to generalizing because of the variation in the raw data. Needless to say, conventional statistical/demographic approaches in medicine cannot tolerate dynamic variation in the data, and either the data is acquired at extremely exacting conditions (e.g., the proper standardized conditions for a blood pressure test), or the variation is simply ignored, with concomitant loss in accuracy.

In the context of providing computer automated assistance in medical health monitoring, there is a significant need for improved approaches to processing and analyzing sensor and labs data from monitored humans, to provide accurate, actionable and early detection and diagnosis of incipient health problems. More particularly, what is needed is a system for leveraging existing sensor measurements to provide better computer automated vigilance of human health problems and to accurately prioritize which patients require the attention of human medical expertise. Improved automated monitoring would provide tremendous benefit in leveraging limited expert medical staff and improving overall healthcare delivery quality and efficiency.

SUMMARY OF THE INVENTION

The present invention provides a novel method and apparatus for computer automated monitoring of human health, such as in an intensive care unit or in long-term health monitoring. Accordingly, sensor data representing measurements of human vital signs and other biological parameters or bodily chemistry are monitored in the present invention to provide early warning of incipient health problems, to provide insight to the medical practitioner into what parameters are deviating from normal behavior, and to provide prioritization for the attention of the medical practitioner. Advantageously, the invention detects and aids in diagnosis of health problems with greater sensitivity and low false alert rate, and increases the patient monitoring load that a given level of medical staff can handle. The invention also greatly facilitates long term and remote human health monitoring by providing earlier and more accurate automated problem detection and diagnosis.

In contrast to conventional methods, which apply thresholds or rules to single parameters (e.g., range of healthy blood pressure), in the present invention, multiple biological parameters are measured and analyzed using a model of normal multivariate variation. More particularly, a series of observations of multiple biological parameters is input to an empirical model of normal behavior for those parameters, which outputs an estimate of what the parameters should be. The estimates are compared to the actual measured values to provide differences, or residuals, for each parameter. Instead of applying thresholds, rules or statistics to raw measured values as is done conventionally, health problems are revealed by analyzing the residuals provided by the model. Thresholds, rules, and statistics can be applied to the residuals to determine whether an incipient disease condition or health problem exists, allowing earlier detection and treatment. By performing analysis on the residual data instead of the raw data, the present invention importantly accommodates normal biological variation in the measured parameters, thus providing more sensitive detection of genuine deviations, at a lower false alert rate.

The empirical model of the present invention is generated using data representative of normal variation of biological parameters in healthy humans. More particularly, kernel-based techniques can be used to provide models of normal dynamic behavior based on multivariate examples from healthy humans. The model generates estimates of values for biological parameters responsive to input of actual measurements of those biological parameters, representative of the normal state closest to the state of the actual measurements. Comparison of the actual measurements to the estimates yields residuals that ideally should be around zero. If the residuals become larger than usual, either in variance or bias (drift), this is indicative of an incipient problem with the parameter corresponding to that residual.

Further according to the invention, patterns and trends of residual deviations can be associated with particular known developing health problems for purposes of diagnostics. Thresholds can be applied to residuals to trigger alerts. Rules can be used to combine residual deviation information into an integrated picture of what underlying disease mechanism is at work, or to rule out certain suspected conditions. Statistics can be applied to time series of residuals to identify trends.

According to an embodiment of the invention, a health monitoring center receives biological parameter data from instruments on patients being monitored for health status. The center may be located in a ward of a hospital, or it may be located offsite and networked to a number if disparately located hospitals or clinics. The set of parameter measurements from each patient is input to one or more empirical models that have been trained to learn normal variation for those biological parameters. Each model generates estimates that are compared to the actual measurements to generate residuals for each given patient. The residuals are available for inspection to medical personnel staffing the center; however automated tests and analyses are carried out in the computer system on the residuals to map the residuals to alerts and diagnoses, which are presented to medical staff. Medical staff utilizes the results of the analyses and alerts to prioritize their manual investigations of patient condition, and to order treatment of any disease conditions identified by the alerts and diagnoses. Medical staff can confirm or dismiss alerts, or cause the empirical models to adapt to and incorporate certain designated actual measurements into the model.

In another embodiment, a person to be monitored in their home living environment is provided with instruments for making either sporadic or real-time measurements of biological parameters, and for transmitting such data to a remote computing center. Data are first used to generate a personalized model of the person (a generic model is also contemplated in the alternative), and after a certain time, the model is used to analyze subsequently sent data. Monitored data results in residuals and corresponding alerts and diagnostics. Monitored data and analysis results are made available over a website to the person's doctor, who can review it and contact the person for more information, to ask the person to come for an examination, or to modify treatment regimens.

In another embodiment, a person engaged generically in a "mission" whose health status is relevant to the mission is instrumented with sensors for measuring biological parameters, and is outfitted with a computing device for analyzing such data according to the invention. Further, the person has a communication device coupled to the computing device for transmitting health status indications resulting from the model-based and residual-based analysis, to a remote location. Mission management uses the health status information for mission decisions.

A variety of biological parameters are amenable to modeling and analysis according to the invention. Typical biological parameters such as ECG, respiration parameters, blood oxygenation and pulse oximetry data, blood pressure, and the like, can be used. Additionally, features derived from these measurements, e.g., heart rate variation, can also provide inputs to the modeling in the present invention.

BRIEF DESCRIPTION OF THE DRAWINGS

The novel features believed characteristic of the invention are set forth in the appended claims. The invention itself, however, as well as the preferred mode of use, further objectives and advantages thereof, is best understood by reference to the following detailed description of the embodiments in conjunction with the accompanying drawings, wherein:

DETAILED DESCRIPTION OF THE PREFERRED EMBODIMENTS

Figure 1:
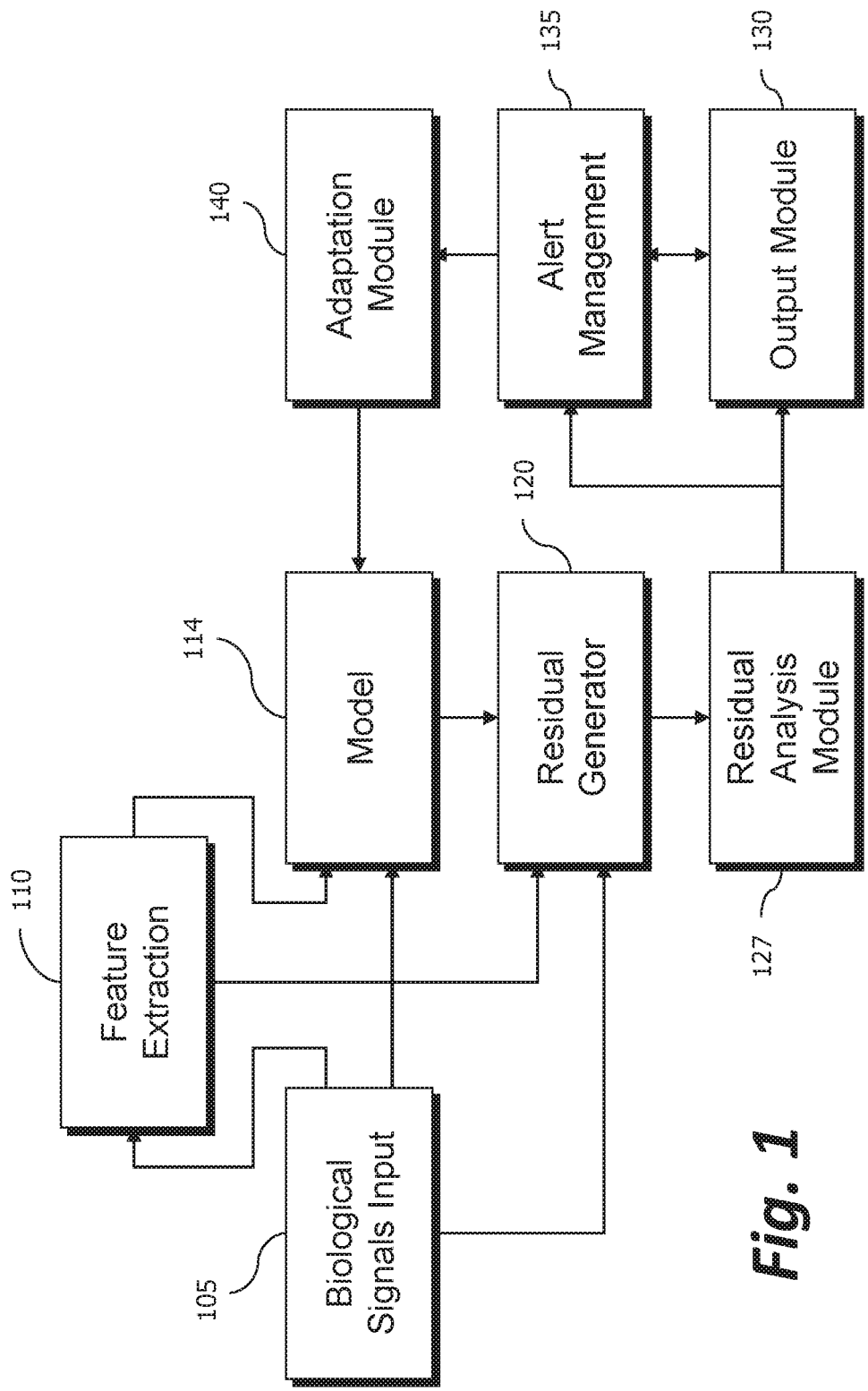
FIG. 1 shows a general arrangement according to one embodiment for carrying out the present invention.

The present invention generally provides for the automated monitoring of human health status and detection of conditions indicative of deteriorating health or of illness, by means of model-based analysis of multiple biological parameters. Accordingly, a model is provided that models normal dynamic variation and interrelationships between the parameters, and generates estimates of those parameters responsive to receiving a set of actual measurements. By way of example, a model may comprise the heart rate, heart rate variability, respiration rate, oximetry, blood pressure, temperature and the like. Measurements of those parameters are input to a model, which generates estimates for those same parameters, representing what those parameters should be, given the integrated picture of the actual measurements. The estimates are differenced with each actual measurement to provide residuals for each parameter. Under normal circumstances, the residuals should be around zero (even if the raw data are dynamically varying over time); if a health problem is developing, the residuals for one or more impacted parameters are likely to become biased or have increasing variance. Computer logic rules—from simple thresholds to complex expert rules—can be applied to the residuals to determine persistence/confidence regarding a deviation indicative of a health problem. Alerts can be generated there from and provided to medical personnel responsible for monitoring the person from whom the data was measured. Alerts can comprise simple notifications of a deviation, or can comprise a diagnosis of a condition requiring intervention. Logic rules can also be used to generate an assessment of disease progression, i.e., a continuous severity rating for a disease condition in a monitored person.

Advantageously, these alerts, diagnoses and assessments based on the residual-based approach of the present invention are more accurate, more sensitive and more reliable than the application of thresholds, rules and other techniques of the prior art to raw data. By providing a model that is capable of making estimates over a range of normal variation of a biological system such as a human, it is possible to remove normal variation and identify a deviation (residuals) at a level considerably smaller than the overall range of normal variation for each instrumented or derived-feature parameter, which would otherwise be lost in the large-scale normal variation.

The model or models used for monitoring human health according to the invention are models of known conditions, and more particularly models of normal conditions of a human (although it may be desirable to model a known condition which is not fully healthy, but known to be stable given the condition of the patient, e.g., post-operative stable). A model for use in the invention is disposed to output an estimate of certain biological parameters based on an input of certain biological parameters. In one embodiment, the estimated parameters correspond to the input parameters and the model is "autoassociative". In another embodiment, the model makes estimates for one or more parameters that are not provided as input to the model, in which case the model is "inferential". The parameters estimated from an inferential model are still compared to actual measurements made of those parameters; only the actual measurements aren't included in the input to the model.

A suitable model for the present invention is an empirical model, since the exact relationships between parameters are often too poorly understood in the human biological system to be the basis for a first-principles model. Further, a suitable empirical model can be a kernel-based model, wherein a mathematical kernel is used to generate estimates of the biological parameters in question based on the input observation and exemplar observations stored in memory. The exemplar observations form a library for kernel-based methods, which embodies the normal combinations of values that are seen in a healthy or stable state person; the kernel operation itself relates these exemplar observations to the input observation and produces an estimate of what would be normal, given the input values. In this way, empirical data (i.e., the exemplar observations) is used to generate an accurate estimation model for parameters for which the interrelationships are not explicitly known.

The invention can be embodied in a computer program executed on one or more computers. In one embodiment, a standalone computer runs a program dedicated to monitoring one person, e.g., on a home computer, and is disposed to receive sensor data from instrumentation either attached on and/or implanted in the person via a communication protocol (e.g., Bluetooth, WLAN), or from measurement station(s) which the person utilizes periodically; and is further disposed to process the data with the model-based, residual-based approach of the present invention and present the data to the person locally and/or upload it to a remote reporting station, e.g., email to or web page available for a doctor, or the like. In another embodiment, hospital ICU equipment is connected to a data station in the ward, which forwards that data for multiple patients to a processing center with one or more computers running programs to analyze the data according to the invention; whereupon the resulting processed data, alerts and diagnoses, etc., are relayed to display screens at the hospital and/or at remote monitoring centers for observation by medical staff. In yet another embodiment, a person with sensor instrumentation attached to or implanted in the body, also carries a small computing platform, such as a personal digital assistance (FDA), which receives the data and processes it locally with the model-based, residual-based approach of the invention to produce results that can be reported locally and/or transmitted to a remote location for viewing by medical staff.

Turning to FIG. 1, a block diagram shows in overview an embodiment of the present invention for monitoring persons with biological parameters sensors or "feature" data streams derived from sensor data. A source of biological signals, 105, provides readings of multiple biological parameters to a model module 114, and optionally a feature extraction module 110. The feature extraction module 110 may provide, for example, heart rate data based on a data feed of an ECG signal from input source 105. Other features are described herein below that may be computed by the feature extraction module 110.

The model 114 generates estimates of certain biological parameters that are desirably monitored. In an autoassociative embodiment, the estimates generated correspond to the inputs from input source 105 (and/or the features generated there from by feature extraction module 110). In an inferential embodiment, the model 114 may generate one or more values that correspond to biological parameters not present in the input, but related to the input in some way previously learned by the model. Subsequently, the estimates from model 114 are made available to a comparison module 120 that generates residuals from the difference of the estimates to the actual values measured, which are provided from input source 105.

The resulting residuals are provided to an analysis module 127 which performs any of a variety of tests on the residuals to determine health-pertinent diagnoses, alerts, severities and the like. This analysis module may execute a rules engine for assessing rules logic using one or more residual values. The rules can be of any of a variety of commonly used rules, from simple univariate threshold measures, to multivariate and/or time series logic. Furthermore, the output of some rules may be the input to other rules, as for example when a simple threshold rule feeds into a windowed alert counting rule (e.g., x threshold alerts in y observations). Furthermore, statistical techniques may be used on the residual data to derive other measures and signals, which themselves can be input to the rules. Applicable statistical analyses can be selected from a wide variety of techniques known in the art, including but not limited to moving window statistics (means, medians, standard deviations, maximum, minimum, skewness, kurtosis, etc.), statistical hypothesis tests, trending and statistical process control (CUSUM, S-chart, etc.).

The residual analysis module 127 provides as output the results of the application of logic rules and statistical tests, which include alerts, diagnostic conclusions and severity ratings. These are provided to an output module 130, which may include means for displaying these results (e.g., computer screens, PDA screens, print outs, or web server), means for storing the results (e.g., a database with query capability, flat file, XML file), and a means for communicating the results to a remote location or to other computer programs (e.g., software interface, XML datagram, email data packet, asynchronous message, synchronous message, FTP file, service, piped command and the like).

An alert management module 135 may also be provided that allows medical staff to annotate and augment the results from the residual analysis module 127, to prioritize results, dismiss or put on hold certain alerts or diagnoses, and otherwise register with the system the responses taken to the results. In addition, there may be data from input source 105 which was analyzed by the model 114, residual generator 120 and residual analysis module 127 as anomalous which medical staff may deem normal, and which needs to be incorporated into the model 114. Alert management module 135 therefore may also provide identification of the data segment to an optional adaptation module 140 that is tasked with incorporating that data into the learning of model 114. In addition, adaptation module 140 may optionally perform its own automated tests on the data and residual analysis results to update the model 114.

As previously mentioned, a multivariate model of the normal or baseline dynamics according to the invention may be an empirical model created from reference data. A preferred form of the model for use in the present invention is an autoassociative or inferential form of the general kernel-based estimator. The autoassociative form is generally:

$$x_{est} = \sum_{i=1}^{L} c_i K(x_{new}, x_i) \qquad (1)$$

where the autoassociative estimate vector Xest of biological parameters is generated from the linear combination of $C_i$ and results from a kernel function K, which compares the input vector Xnew of biological parameter measurements (or features), to L learned patterns or exemplars of such measurements, Xi. To provide a multivariate estimate vector Xest, the $C_i$ are vectors, and can be determined according to a number of different methods that gives rise to variations on kernel-based estimators, and may be functions in part of the input Xnew and/or the exemplars Xi. The learned patterns come from the class of "data behavior" on which the model is trained, e.g., normal or healthy humans, or post-operative stable condition. As will be described in further detail herein below, the exemplars may be particularly chosen to represent normal conditions for a specific human type based on age, gender, weight, condition, etc., or a combination thereof, such that for purposes of monitoring, say, an elderly female patient, the model may be a model of normal biological parameters for an elderly female based on the exemplars obtained from that population, by way of example.

The inferential form of the general kernel-based estimator is:

$$y_{est} = \sum_{i=1}^{L} c_i K(x_{new}, x_i) \qquad (2)$$

where a vector Y of biological parameter values is estimated from the kernel-based comparison of the input vector of other biological parameters $X_{new}$ to the L learned exemplars of those parameters, Xi. Each learned exemplar $X_i$ is associated with another exemplar vector $Y_i$ of the parameters to be estimated, which are combined in a weighted fashion according to the kernel K and vectors Ci (which are functions at least in part of the Yi) to predict output Y.

What is common to the kernel-based estimators is the kernel function, and the generation of a result from a linear combination of exemplars, based on the kernel results and the vectors Ci that embodies the exemplars. Kernel function K is a generalized inner product, but preferably has the further characteristic that its absolute value is maximum when Xnew and Xi are identical.

According to one embodiment of the invention, a kernel-based estimator that can be used to provide the model is Kernel Regression, exemplified by the Nadaraya-Watson kernel regression form:

$$y_{est} = \frac{\sum_{i=1}^{L} y_i^{out} K(x_{new}, x_i^{in})}{\sum_{i=1}^{L} K(x_{new}, x_i^{in})} \quad \text{(Inferential form)} \qquad (3)$$

$$x_{est} = \frac{\sum_{i=1}^{L} x_i K(x_{new}, x_i)}{\sum_{i=1}^{L} K(x_{new}, x_i)} \quad \text{(Autoassociative form)} \qquad (4)$$

In the inferential form, a multivariate estimate of inferred biological parameters Yest is generated from the results of the kernel K operator on the input vector of parameter measurements Xnew and the L learned exemplars Xi, linearly combined according to respective learned vectors Yi, which are each associated with each Xi, and normalized by the sum of kernel results. The Yi represent the L sets of learned measurements for the parameters in Y, which were associated with (i.e., measured contemporaneously with) the learned measurements of parameters in X. By way of example, X may comprise a plurality of arterial blood pressure readings, while Y may represent a corresponding plurality of peripheral blood pressure readings.

In the autoassociative form of the kernel regression, a multivariate estimate of biological parameters Xest is generated by a normalized linear combination of the learned measurements of those parameters Xi, multiplied by the kernel operation results for the input vector Xnew vis-á-vis the learned observations Xi.

In kernel regression for purposes of the invention, it can be seen that the Ci from equations 1 and 2 above are composed of the learned exemplars normalized by the sum of the kernel comparison values. The estimate vectors, Yest or Xest, comprise a set of estimated parameters that are, according to the invention, differenced with actual measured values (Xnew, or Ynew, which is not input to the model in the inferential case) to provide residuals.

In another embodiment, a similarity-based model (SBM) can be used as the model according to the present invention. Whereas the Nadaraya-Watson kernel regression provides estimates that are smoothed estimates given a set of (possibly noisy) learned exemplars, SBM provides interpolated estimates that fit the learned exemplars when they also happen to be the input as well, i.e., if the input vector is identical to one of the learned exemplars. This can be advantageous in detecting deviations in biological parameters, since noise in these signals will be overfit to a certain extent (if noise was similarly present on the exemplars from which the model was made), thus removing the noise somewhat from the residuals as compared to the kernel regression approach. SBM can be understood as a form of kernel-based estimator by rewriting the kernel function K as the operator $\otimes$, and equating the set of learned exemplars Xi as a matrix D with the elements of Xi forming the rows, and the Xi observations forming its columns. Then:

$$K_{i=1}^{L}(x_i, x_{new}) = (D^T \otimes x_{new}) \quad (5)$$

where D has been transposed, which results in a column vector of kernel values, one for each observation Xi in D. Similarly, the comparison of all exemplars with each other can be represented as:

$$K_{i,j=1}^{L}(x_i, x_j) = (D^T \otimes D) \quad (6)$$

Then, the autoassociative form of SBM generates an estimate vector according to:

$$x_{est} = D \cdot (D^T \otimes D)^{-1} \cdot (D^T \otimes x_{in}) \quad (7)$$

where X(est) is the estimate vector, X(in) is the input observation (shown above as Xnew), and D is a learned vector matrix comprising the set (or subset) of the learned exemplary observations of the biological parameters. The similarity operation or kernel is signified by the symbol $\otimes$, and has the general property of rendering a similarity score for the comparison of any two vectors from each of the operands. Thus the first term ($D^T \otimes D$) would yield a square matrix of values of size equal to the number of observations in D as shown in equation 6. The term ($D^T \otimes x_{in}$) would yield a vector of similarity values, one for each vector in D as shown in equation 5. This similarity operator is discussed in greater detail below.

The estimate can further be improved by making it independent of the origin of the data, according to the following equation, where the estimate is normalized by dividing by the sum of the "weights" created from the similarity operator:

$$x_{est} = \frac{D \cdot (D^T \otimes D)^{-1} \cdot (D^T \otimes x_{in})}{\sum ((D^T \otimes D)^{-1} \cdot (D^T \otimes x_{in}))} \quad (8)$$

In the inferential form of similarity-based modeling, the inferred parameters vector Yest is estimated from the learned observations and input according to:

$$y_{est} = D_{out} \cdot (D_{in}^T \otimes D_{in})^{-1} \cdot (D_{in}^T \otimes x_{in}) \quad (9)$$

wherein the matrix of learned exemplars D can be understood as:

$$D = \begin{bmatrix} y_1 & y_2 & y_3 & \cdots & y_L \\ x_1 & x_2 & x_3 & \cdots & x_L \end{bmatrix} = \begin{bmatrix} D_{out} \\ D_{in} \end{bmatrix} \quad (10)$$

Normalizing as before using the sum of the weights:

$$y_{est} = \frac{D_{out} \cdot (D_{in}^T \otimes D_{in})^{-1} \cdot (D_{in}^T \otimes x_{in})}{\sum ((D_{in}^T \otimes D_{in})^{-1} \cdot (D_{in}^T \otimes x_{in}))} \quad (11)$$

Yet another kernel-based modeling technique similar to the above that can be used according to the invention is the technique of radial basis functions. Based on neurological structures, radial basis functions make use of receptive fields, in a special form of a neural network, where each basis function forms a receptive field in the n-dimensional space of the input vectors, and is represented by a hidden layer node in a neural network. The receptive field has the form of the kernels described above, where the "center" of the receptive field is the exemplar that particular hidden unit represents. There are as many hidden unit receptive fields as there are exemplars. The multivariate input observation enters the input layer, which is fully connected with the hidden layer. Thus each hidden unit receives the full multivariate input observation, and produces a result that is maximum when the input matches the "center" of the receptive field, and diminishes as they become increasingly different (akin to SBM described above). The output of the hidden layer of receptive field nodes is combined according to weights $c_i$ (as above in equation 1).

All of the above methods for modeling according to the present invention utilize the aforementioned kernel-based approach and utilize a library of exemplars. The exemplars (also called reference observations or reference vectors) represent "normal" behavior of the modeled system as seen by means of the modeled biological parameters. Optionally, the available reference data can be down-selected to provide a characteristic subset to serve as the library of exemplars, in which case a number of techniques for "training" the kernel-based model can be employed. According to a preferred training method, at least those observations are included in the library that have a highest or lowest value for a given biological parameter across all available reference observations. This can be supplemented with a random selection of additional observations, or a selection chosen to faithfully represent the scatter or clustering of the data.

Alternatively, the reference data may be clustered, and representative "centroids" of the clusters formed as new, artificially generated exemplars, which then form the library. A wide variety of techniques are known in the art for selecting the observations to comprise the library of exemplars.

As mentioned above, the kernel can be chosen from a variety of possible kernels, and preferably is selected such that it returns a value (or similarity score) for the comparison of two identical vectors that has a maximum absolute value of all values returned by that kernel. While several examples are provided herein, they are not meant to limit the scope of the invention. Following are examples of kernels/similarity operators that may be used according to the invention for the comparison on any two vectors $X_a$ and $X_b$.

$$K_h(x_a, x_b) = e^{-\frac{\|x_a - x_b\|^2}{h}} \quad (12)$$

$$K_h(x_a, x_b) = \left(1 + \frac{\|x_a - x_b\|^\lambda}{h}\right)^{-1} \quad (13)$$

$$K_h(x_a, x_b) = 1 - \frac{\|x_a - x_b\|^\lambda}{h} \quad (14)$$

In equations 12-14, the vector difference, or "norm", of the two vectors is used; generally this is the 2-norm, but could also be the 1-norm or p-norm. The parameter h is generally a constant that is often called the "bandwidth" of the kernel, and affects the size of the "field" over which each exemplar returns a significant result. The power $\lambda$ may also be used, but can be set equal to one. It is possible to employ a different h and $\lambda$ for each exemplar Xi. Preferably, when using kernels employing the vector difference or norm, the measured data should first be normalized to a range of 0 to 1 (or other selected range), e.g., by adding to or subtracting from all sensor values the value of the minimum reading of that sensor data set, and then dividing all results by the range for that sensor. Alternatively, the data can be normalized by converting it to zero-centered mean data with a standard deviation set to one (or some other constant). Furthermore, a kernel/similarity operator according to the invention can also be defined in terms of the elements of the observations, that is, a similarity is determined in each dimension of the vectors, and those individual elemental similarities are combined in some fashion to provide an overall vector similarity. Typically, this may be as simple as averaging the elemental similarities for the kernel comparison of any two vectors x and y:

$$K(x, y) = \frac{1}{L}\sum_{m=1}^{L} K(x_m, y_m) \quad (15)$$

Then, elemental similarity operators that may be used according to the invention include, without limitation:

$$K_h(x_m, y_m) = e^{-\frac{|x_m - y_m|^2}{h}} \quad (16)$$

$$K_h(x_m, y_m) = \left(1 + \frac{|x_m - y_m|^\lambda}{h}\right)^{-1} \quad (17)$$

$$K_h(x_m, y_m) = 1 - \frac{|x_m - y_m|^\lambda}{h} \quad (18)$$

The bandwidth h may be selected in the case of elemental kernels such as those shown above, to be some kind of measure of the expected range of the mth parameter of the observation vectors. This could be determined, for example, by finding the difference between the maximum value and minimum value of a parameter across all exemplars. Alternatively, it can be set using domain knowledge irrespective of the data present in the exemplars or reference vectors, e.g., by setting the expected range of a heart rate parameter to be 40 to 180 beats per second on the basis of reasonable physiological expectation, and thus h equals "140" for the mth parameter in the model which is the heart rate. Furthermore, it should be noted with respect to both the vector and elemental kernels that use a difference function, if the difference divided by the bandwidth is greater than 1, it can be set equal to one, resulting in a kernel value of zero for equations 13, 14, 17 and 18, for example. Also, it can readily be seen that the kernel or similarity operator can be modified by the addition or multiplication of different constants, in place of one, h, $\lambda$, and so on. Trigonometric functions may also be used, for example:

$$K_h(x_m, y_m) = \left(1 + \sin\left(\frac{\pi}{2h}|x_m - y_m|\right)\right)^{-1} \quad (19)$$

Most preferably, the similarity operation or kernel generally provides a similarity score for the comparison of two identically-dimensioned vectors, which similarity score:
1. Lies in a scalar range, the range being bounded at each end;
2. Has a value of one of the bounded ends, if the two vectors are identical;
3. Changes monotonically over the scalar range; and
4. Has an absolute value that increases as the two vectors approach being identical.

In an important alternative embodiment of the invention, both the inferential and autoassociative forms of the empirical kernel-based model can be generated "on-the-fly" based on qualities of the input observation, and drawing from a large set of learned observations, i.e., a reference set. This process is called localization. Accordingly, it is a preferred form of the invention that the above described calculations for the inferential and autoassociative forms of kernel-based modeling can be carried out using a set of learned observations $x_i$ or D that are selected from a larger set of reference observations, based on the input observation. Kernel-based models are exceptionally well suited for this kind of localization because they are trained in one pass and can be updated rapidly. Advantageously, by drawing on a large set of candidate exemplars, but selecting a subset with each new input observation for purposes of generating the estimate, the speed of the modeling calculation can be reduced and the robustness of the model improved, while still well characterizing the dynamics of the system being modeled.

Figure 2:
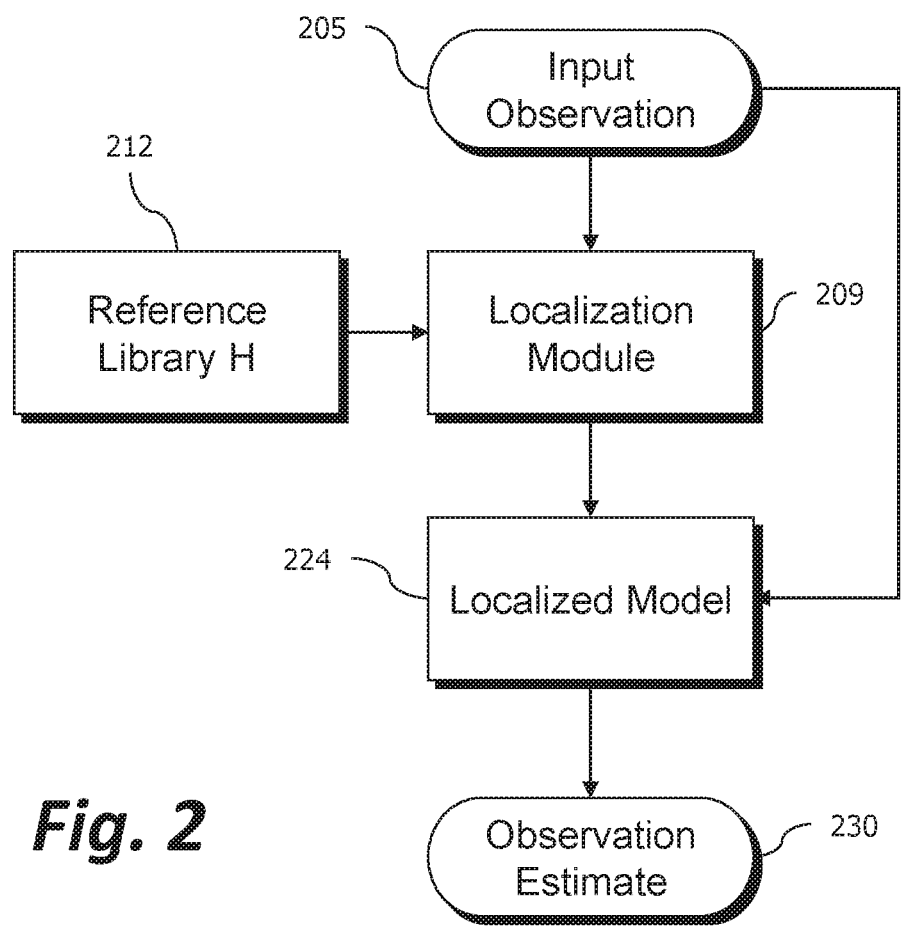
FIG. 2 shows a flowchart for localization of the model according to one embodiment of the invention.

A variety of criteria can be used to constitute the localized D matrix membership, including the application of the similarity operator itself. In general, however, the process can be understood with reference to FIG. 2. The input observation 205, comprising the set of biological parameters or derived features that are to be estimated by the model as part of the monitoring process, are provided to a localization module 209, which accesses a large store of exemplar observations in the form of a reference library 212, in order to select a subset of those exemplar observations to constitute the model. Localization module 209 selects exemplars from library 212 that are relevant to the input observation 205, which can be a much smaller set than the size of the library. By way of example, the reference library 212 might comprise 100,000 exemplar observations that characterize the normal dynamics of the biological system represented by the parameters being modeled, but the localization module 209 might select only a few dozen observations to build a localized model in response to receiving the input observation 205. The selected exemplar observations are then provided to the localized model 224, and these observations then comprise the set of learned exemplars Xi for purposes of the kernel-based estimator (also shown as D in connection with SBM above). The estimate observation 230 is then generated accordingly as described above. As the next input observation 205 is presented to the monitoring system of the invention, the process is repeated, with selection of a new and possibly different subset of exemplars from library 212, based on the new input observation.

According to one embodiment of the invention, the input observation 205 can be compared to the reference library 212 of learned observations, on the basis of a clustering technique. Accordingly, the exemplar observations in library 212 are clustered using any of a number of techniques known in the art for clustering vectors, and the localization module 209 identifies which cluster the input observation 205 is closest to, and selects the member exemplars of that cluster to be the localized observations provided to the localized model 224. Suitable clustering methods include k-means and fuzzy c-means clustering, or a self-organizing map neural network.

According to another embodiment of the invention, a kernel can be used to compare the input observation 205 to each exemplar in the library 212 to yield a similarity value that provides a ranking of the reference observations vis-á-vis the input observation. Then, a certain top fraction of them can be included in the localized D matrix. As a further refinement of this localization aspect, observations in the ranked list of all reference observations are included in localized D to the extent one of their component elements provides a value that "brackets" the corresponding value in the input vector, even if other observations in library 212 have higher similarity to the input. This search down the ranked list is performed until either all values in the input vector are bracketed on both the low and high side by a value in one of the reference observations included in localized D, or until a user-selectable maximum limit of vectors to include in D is reached, or until there are no further reference observations that have sufficiently high similarity to the input to surpass a similarity threshold for inclusion.

Other modifications in determining the membership of localized D are within the scope of the invention. By way of example, in both the clustering selection method and the similarity selection method described above, the set of elements, i.e., parameters used to comprise the vectors that are clustered or compared with the kernel for similarity, may not be identical to those used to generate the model and the estimate, but may instead be a subset, or be a partially overlapping set of parameters. For instance, in monitoring a patient according to the invention with a set of a half-dozen or more biological parameters and features such as heart rate, respiration volume, blood pressure(s), temperatures and the like, localization could be performed utilizing only heart rate and respiration parameters.

Figure 3:
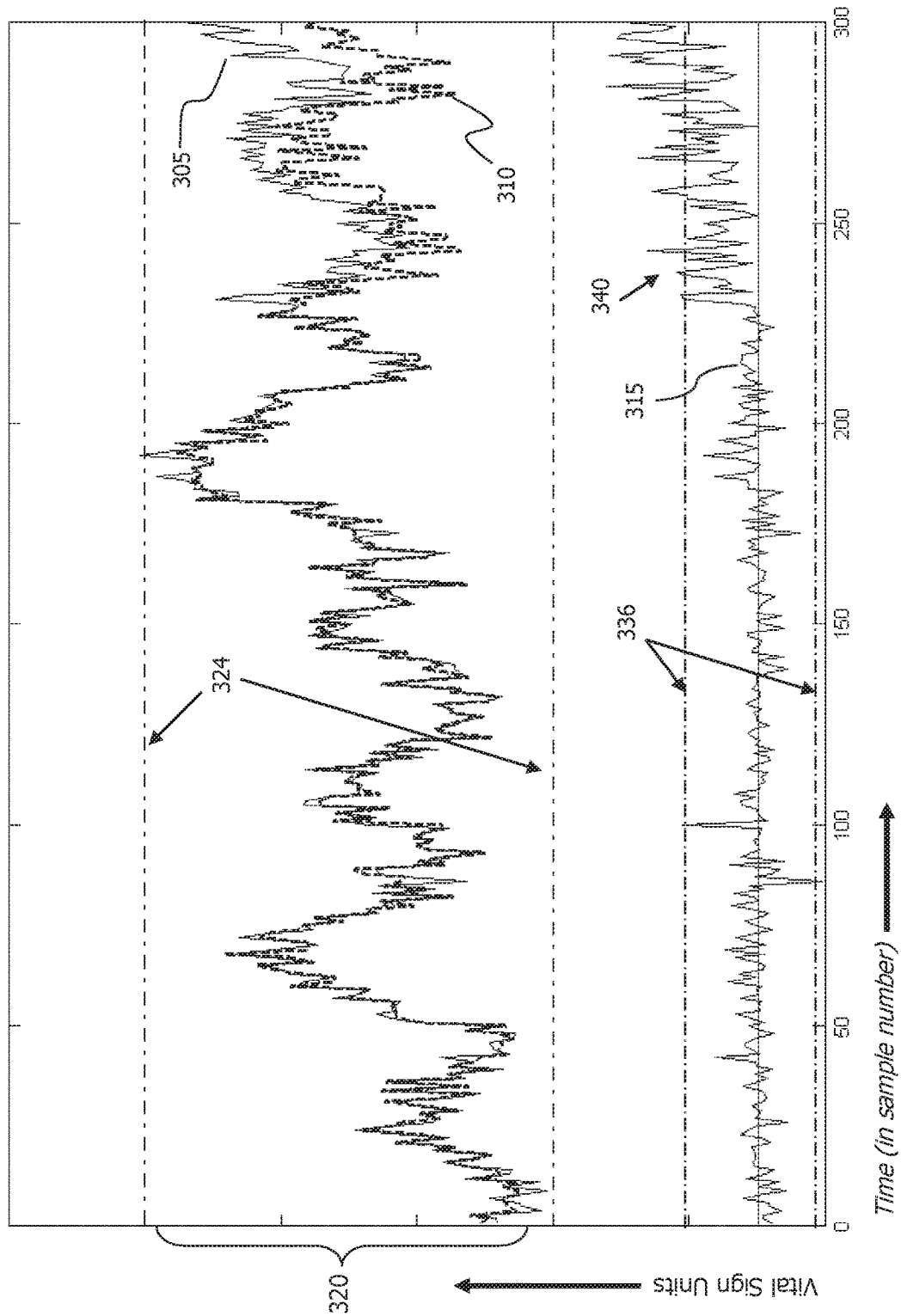
FIG. 3 shows a chart having a signal, its estimate and a residual signal, as generated according to the present invention.

Turning to FIG. 3, the approach of the present invention can be better understood in view of an arbitrary charted raw signal 305, which may represent any biological parameter being modeled, and its estimate 310, and the corresponding residual 315 plotted in the bottom half of the chart. The signal 305 is one of multiple parameters being modeled (either autoassociatively or inferentially), though the other signals are not shown in the figure. It may be seen that the raw signal exhibits variation and has a range 320, which is typical of biological systems where a biological parameter may vary due to environment, activity, metabolism, diurnal timing, etc. In conventional approaches, limits 324 are provided for detecting when signal 305 goes outside an acceptable range deemed normal or healthy. Consequently, problems may remain undetected until a later time, when the signal 305 goes outside the limits 324. However, by providing a model-generated estimate 310 of the parameter 305, and differencing them to produce residual 315, alternative residual limits 336 can be used to detect when the signal 305 is deviating from what is expected, even as signal 305 varies throughout its normal range 320. Consequently, detection of abnormal values can be achieved at a significantly earlier time 340, even when the signal 305 is still well within its normal range 320.

Advantageously, by analyzing the residuals provided by the invention, better diagnostics and alerting is possible compared to application of the same analysis to raw data. A wide variety of statistical, logical and mathematical techniques can be used to analyze the residuals for each biological parameter monitored according to the invention, which are now discussed for purposes of illustration.

A first technique that may be used is to apply a threshold to the residual for a parameter. Whereas in conventional medicine, a threshold is typically applied to raw data, a residual threshold is capable of a much tighter limit without resulting in a higher false alert rate, because normal variation has been removed by differencing the estimate and the actual data. A residual threshold can be an upper limit, a lower limit, or both, and an alert is registered when the residual exceeds the threshold. The threshold can be determined from domain expertise, or can be set as a function of the noise distribution for the residual data for a particular parameter. For example, a particular measurement device may provide exceptionally noisy raw data, such that the residual has a correspondingly higher noise level. This noise level can be observed for a sufficient number of observations to characterize the distribution of the residual signal, whereupon the threshold is set as a function of this revealed distribution (such as 5× the standard deviation), thereby accommodating the noise level of the measurement device. Each biological parameter on each patient monitored may have its own set threshold level, A threshold is just a simple form of a rule in a rules system or expert system. Such a system can extend the flexibility and power of the analysis of residuals according to the invention. For example, a simple threshold may be extended to a rule for triggering a deviation detection alarm when the residual has exceeded the threshold a sufficient number of times in a moving window of observations (an x alerts in y observations rule). An alarm or notification can also be configured for a combination of conditions on residuals across more than one parameter. For example, a notification of the possibility of health condition may be generated by the monitoring system of the invention when one residual signal exceeds its upper limit and another residual signal exceeds its lower limit. Multivariate rules may also utilize a time series of observations of residuals. Rules themselves may be chained together to trigger other rules, or to veto the results of other rules. A wide variety of expert rules systems are known in the art for dealing with raw data, and these rules structures can be readily adapted for the present invention by translating them into rules for residuals. For example, whereas a prior raw data rule structure may have indicated a possible health threat when a certain parameter is more than two standard deviations above the "average" value for the population (a conventional distribution approach), the new rule may provide the same notification when the residual is more than two standard deviations (or some other threshold) away from zero for that residual signal (where the standard deviation may be determined from the signal derived from that patient, or may be derived from experiments where people have been monitored with that parameter and that model in preparing the model for clinical use). Series of residual values for a parameter form a signal, which signal can be treated with various statistical techniques for trending and hypothesis testing, as mentioned above. Statistical hypothesis tests such as Wald's sequential probability ratio test may be used.

A variety of pattern recognition techniques can further be used to associate a pattern of residuals to an alert, a diagnostic conclusion, or a severity rating for a patient's condition. One such technique is to provide a set of residuals for a plurality of monitored parameters to a neural network that has been trained to associate the inputs with diagnostic conditions.

Turning to the selection of biological parameters that may be modeled for the monitoring purposes of the present invention, the advantages in detection sensitivity and accuracy of the invention are due, among other things, to the multivariate approach taken to the biological parameters, in contrast to conventional medical practices where parameters are tested in isolation. Accordingly, using the kernel-based estimators of the present invention, the observations of biological parameters are multivariate in that each observation generally comprises a data value (whether a direct sensor reading or some derived feature of sensor data) for each of multiple parameters, attributed to an approximately contemporaneous instant or period. For example, the observations can comprise snapshots of several parameter data values at instants of time. Importantly, the kernel-based methods of the present invention do not require that the snapshots are acquired periodically, but rather they can be acquired at irregular intervals.

The data values for the biological parameters can therefore be direct sensor measurements, e.g., temperature at a time t, or can be derived features such as instantaneous or window-averaged heart rate as attributed to time t. Because the observations need not be regularly sampled, it is possible to align various regularly sampled signals (ECG, respiration, oximetry, pressures, temperatures, etc.) to identified semi-regular or irregular triggers. In one embodiment, an observation is formed keyed to the QRS peak of the ECG signal, and all other sampled signals are measured as of that time, or over the RR interval (one QRS peak to the next). It is known that heartbeats are somewhat irregular naturally, and thus data values for parameters can be generated as a function of the QRS peak (or any other identifiable point) of the ECG signal. In another embodiment, observations are formed at regular intervals, such as once per minute, and may contain raw values at the minute, statistics on the signal over the minute, or cumulative or averaged moving window values attributed to each minute measurement. Thus, modelable biological parameters might be selected from (a) raw instantaneous signal values; (b) statistical values from the signal, within a window defined by some other signal event (like QRS peak); (c) cumulative; averaged statistical value from the signal, over a set of such windows; (d) rate of change of one of the above, from last window to current window; and (e) cumulative/averaged measures from a signal over a regular time window (e.g., once per minute).

For purposes of illustration, features that may be derived for use in a kernel-based model for monitoring human health, using a keying event like the QRS peak of the ECG signal, include:

Instantaneous Heart Rate—Time from last QRS peak, or time to next QRS peak.

Blood Pressure "Systolic"—Highest blood pressure reading from a continuous blood pressure measurement device (catheterized or non-invasive) in the window from the current QRS peak to the next (or to the last) QRS peak in the ECG.

Blood Pressure "Diastolic"—Lowest blood pressure reading from a continuous blood pressure measurement device (catheterized or non-invasive) in the window from the current QRS peak to the next (or to the last) QRS peak in the ECG.

"Systolic" BP Lag—Time between QRS peak and next "systolic" (i.e., highest) peak in blood pressure signal from continuous BP measurement sensor.

"Diastolic" BP Lag—Time between QRS peak and next "diastolic" (i.e., lowest) trough in blood pressure signal from continuous BP measurement device.

Oxygen Saturation Peak (Ebb)—Highest (lowest) measurement of oxygen saturation (SpO2) between present QRS peak and next QRS peak.

Temperature—Average, maximum, minimum or median value of a temperature sensor, over a window from one QRS peak to the next.

If the respiration cycle is used as the keying event for data collection, the following parameters are further illustrative of parameters that may be used:

Instantaneous Respiration Rate—Time from one complete breath to the next.

Heart beat count—Number of heartbeats within one complete breath.

Oxygenation lag—Time lag between some point in the breathing cycle, e.g., end of inhalation, and the peak of the blood oxygenation signal from, e.g., an oximeter.

Of course, other statistical measures of the above can be substituted, such as determining the median value, mean value, hi-lo difference (range), etc., of the above parameters or their biological source signal.

Further to illustrate, features that may be derived over a set of windows defined by an event like the QRS peak include:

Windowed Respiration Rate—Respiration rate as measured over the last m windows defined by QRS peak-to-peak (a.k.a. RR intervals). The value is attributed to the observation keyed to the current QRS peak event. Respiration rate can be instantaneous (period of current respiration) or averaged. If the respiration rate is longer than the span of all m windows, an estimate of the complete respiration rate for that respiratory cycle can be generated by extrapolation from the partial cycle.

Windowed Respiration Depth—Maximum volume of breathing as measured over the last m windows defined by QRS peak-to-peak. The value is attributed to the observation keyed to the current QRS peak event.

Heart Rate Variability (SDNN type)—Variance or standard deviation in instantaneous heart rate over last m windows defined by QRS peak-to-peak. Each one of the m windows has an instantaneous heart rate, and the variance or standard deviation is calculated over all m in values.

Heart Rate Variability (RMSSD type)—Square root of the sum of squared successive differences in instantaneous heart rate (or heart beat period), over last m windows.

Other parameters that may be used by way of example can be derived from other devices connected to the patient, such as ventilators. Typical ventilation parameters can be used in a kernel-based model for patient monitoring according to the invention. These include:

Tidal volume (or Minute Volume)—Measure of volume of air exhaled or inhaled (instantaneously or averaged/cumulative over a window, e.g., a minute).

$CO_2$—Measurements of the volume, partial pressure or concentration of exhaled carbon dioxide.

Peak Inspiratory Pressure—Maximum pressure applied during the inspiratory cycle by the ventilator.

Positive End Expiratory Pressure—Baseline positive pressure at the end of expiration. This parameter may be particularly useful as a localizing variable.

FIO2—Fraction oxygen in inspired air, typically a percentage. This variable may also be particularly useful as a localizing variable.

PIF, PEF—Peak inspiratory/expiratory flow of air.

Airway Resistance—Measures of resistance of the lungs to positive pressure ventilation.

In a home telehealth monitoring setting, the subject may be instrumented with a growing variety of sensors, or may be asked to make periodic measurements that can be used in the modeling of the present invention, including:

Weight—Scale-measured body weight of the subject/patient.

Blood Glucose Level—Instruments that sample drops of blood and measure glucose levels of the blood; or instruments that make determinations of glucose levels in the blood from optical measurements.

Activity—Accelerometers may be used to measure the amount of movement of the patient; potentially these can be instrumented to provide movement in certain directions (e.g., up-down versus laterally).

Ambient Temperature Differential—Measures of the difference in temperature between the ambient air and the skin or periphery.

Sweat—Measures of the degree to which the subject is sweating.

The above list of parameters is meant only to be illustrative of the types of variables that can be obtained from a human subject, and which can be used in the kernel-based modeling approach of the present invention. This list is not meant to be limiting. Biological parameters used in the present invention for forming observations can include temperatures, pressures, activity ranges (e.g., breathing volume), rates (respiration, heart), conductivity, electrical activity (e.g., EEGs), chemical measurements, flow rates and any other known or later developed metrics of the human biological system. Preferably, the parameters combined into a model for purposes of monitoring are (a) deemed to be related in some way (whether known or suspected) either as cause-and-effect or joint effects; (b) generally responsive to changes in the body or the body's feedback control loops within approximately equal orders of magnitude time periods; and (c) useful for pointing to root cause if a deviation is found in one or more of them. Preferably, a model according to the invention for monitoring human health includes one or more of a heart rate, a blood oxygenation value, a respiration metric, a blood pressure metric, and a temperature metric. In preferred embodiments of the invention, a model for use in monitoring human health comprises 3 or more parameters, and more preferably 5 or more parameters (raw signals or features derived from signals). Advantageously, the kernel-based modeling approach of the invention is effective with a large number of variables as well, more than 20-30 related parameters.

Due to the disruptive nature of some activity on certain kinds of biological signals, such as how coughing or talking affect the respiration signal, another aspect of the invention is to provide for filtering the input observations. Generally, in the context of a patient recuperating in an ICU, or the like, observations are preferably monitored only when the patient is in a state where the data is well behaved, more specifically when the patient is sleeping or resting, as opposed to talking, coughing, or being moved. A data-filtering module can be provided that automatically recognizes the sleeping or resting states, and filters out other data, leaving only that data from the sleeping/resting state for monitoring. A number of techniques can be used to automatically determine whether the data is coming from a patient in sleeping/resting state. One method that may be used is to process the input observation, or a sequence of input observations, through an inferential model to determine its classification. Such a model can be, for example, an inferential kernel-based model according to the present invention, wherein a single output variable is provided, which ranges between two values (e.g., zero and one) each of which corresponds to "not in class" and "in class" respectively. The model can be trained from examples of normal sleep/rest. Similarly, a wide variety of clustering techniques are known in the art for determining what class the input data is characteristic of, and outputting that classification. By way of example, K-means clustering is a well-known technique that can accept as input a set of observations, and cluster the observations into a user-determined number of clusters; thereafter, new observations can be associated with the appropriate cluster or class. Observations associated with the sleep/rest cluster would then be monitored, whereas observations that did not fit this cluster would be filtered out. Finally, it is known to use expert rules to process the input observation to determine whether it is in the sleeping/resting state or not. Such rules may include determining the heart rate and respiration rate, and after determining that these are within certain ranges, and also determining that the rate of respiration has not changed or skipped an anticipated breath, then the state is sleeping/resting.

Another method for handling disruptive events in the data is to filter them in a number of ways. Typical disruptive events can include an abnormal heartbeat (skipped or extra), or coughing; talking which interrupts the normal profile of a breath. While these are interesting patterns in the data and may be of interest medically, for purposes of modeling and relating these parameters to each other, it is useful to filter them out. Hence, a heart rate can be smoothed by identifying skipped or extra beats and eliminating that data point. One way to do this is to calculate the instantaneous heart rate over R-R intervals, and to apply a filter to the resulting rate signal, such as a median filter with a window of 3-5 data points. As a consequence, the anomalous instant heart rate that may jump high with an extra beat, or drop low upon a skipped beat, is replaced with a median value in a window, which is likely not to be the anomalous value. One way to eliminate nonconforming breathing cycles is to identify a normal breath on either side of the nonconforming region, and excise the data completely. A nonconforming breath cycle can be identified as one that insufficiently matches a prototype breath pattern (e.g., starting in a trough, increasing to a peak, and dropping back to a trough). A number of pattern matching techniques are known in the art for matching a prototype pattern to instant windows on a signal, which techniques can be used for this purpose.

More than one model may be used to monitor the health of a person, and parameters may be shared across models. Accordingly, one embodiment of the invention forms an inferential model for each vital sign or other parameter from the set of all other available parameters; hence the total number of models used is equal to the member of monitored parameters. Furthermore, monitoring of a person can be performed with different models using data sampled at different rates. For example, one model may use data with observations formed by some trigger such as the RR interval, while another model may use observations formed once per minute. As another example, a first model may include such biological parameters as are necessary to monitor cardiovascular function, and a second model may include such biological parameters as are necessary to monitor immunological responses. As yet another example, multiple models of the same parameters may be used, but trained on different activity states or classes. Then, as the input observation is classified according to the type of activity it represents (sleep/rest as above, or exercise, or walking, etc.), a model according to the invention that has learned that class of activity is used to monitor that observation or window of observations.

A particular embodiment of the invention comprises an autoassociative model with observations at intervals of between 10 seconds and 1 minute, and comprising the parameters of average heart rate, average respiration rate, average systolic blood pressure, average diastolic blood pressure, average respiration depth/volume, and average blood oxygenation percentage (oximetry). The heart rate and respiration parameters may be raw signals, or may be smoothed, meaning removal of abnormal (extra or missed) beats or abnormal breathing (coughs, etc.). Also, in place of the average of the above values over the interval, some other statistic, such as the median, maximum or minimum can be used.

The present invention also provides for monitoring of human health using chemical, immunological, microbiological, histological, hematological and similar test results, and more particularly blood constituent measurements, urine constituent measurements and the like (commonly referred to as "lab results" or "labs"). Such measurements can be used to great advantage in the present invention because (a) the measurements typically are multivariate, (b) the multivariate results represent fluid makeup at more or less a single time, and (c) though labs are ordered typically on an irregular basis, the present invention can nonetheless use data sampled in such a non-periodic fashion. A further advantage of the invention over conventional use of labs data is the greater ability to discriminate changes. Conventionally, each measurement of a constituent in blood, for example, is examined in isolation, and compared to a "normal" range for the healthy population. In contrast, according to the present invention, normal dynamics of each constituent vis-á-vis one another are modeled and taken into account, so that even small deviations in the value of a constituent can be detected, though the deviation might still be well within the "normal" range under the conventional approach.

The biological parameters modeled with laboratory results data can include any of a number of typically measured values, including blood sugar (glucose); blood gases such as oxygen, carbon dioxide and bicarbonate; measures of acidity such as pH; measures of breakdown products such as creatinine or blood urea nitrogen (BUN); measures of electrolytes such as sodium, potassium, and chloride; and measures of enzymes and proteins such as creatinine kinase, albumin, C reactive protein, bilirubin; and measures of minerals such as calcium, iron, magnesium, zinc and the like. The learned exemplars of the model can comprise exemplary blood sample test results for a number of healthy individuals in the population, and more particularly those who have similar demographic traits as the person being monitored, since many of these parameters change with gender, age, weight and the like. Consequently, to monitor the labs of a patient who is a young male of normal body weight, a model of normal blood constituent dynamics for a young male of normal body weight may comprise real test results from many such individuals, gathered at various times during the diurnal cycle, sufficient to cover the dynamics of how these parameters vary with respect to one another throughout normal activity and health. When the patient's results are input to the model, the estimate of the parameters based on a variety of learned normal exemplars, is compared to the patient's actual results to generate residuals, and deviations in the residuals may be present that are smaller than the ranges for those parameters in the normal population, but which nonetheless are significant indicators of a health condition (whether incipient and trending worse, or merely a static disease state). If the patient is subject to a series of blood, urine or other fluid tests, these residual results can themselves comprise time series for subsequent analysis according to the invention.

In the context of monitoring a patient in a hospital ward, a nursing home or a clinic, the present invention can be practiced as follows. A patient is instrumented with sensors attached to bedside devices for monitoring vital signs and other biological parameters of the patient. This data is provided from the bedside devices, typically over a computer network, to a computer running software for processing the data according to the invention. The computer stores or has access to stored exemplar data comprising one or more models for use in generating estimates responsive to receiving an observation of sensor data from the patient. Data may also be provided to the computer regarding the results of laboratory tests for the patient, which typically are provided from a hospital information system where the results have been entered. For example, the patient may be monitored with one model for a set of bedside vital signs, at a data sampling frequency on the order of once per minute; and a second model is used to process labs results for the patient, which may be received by the computer at irregular intervals. From each such model as may be used to monitor the data of the patient, estimates for the data are generated, and residuals generated upon comparison of the estimates to the actual values. The computer may be further disposed to apply a variety of post-modeling analytic steps on the residuals, described elsewhere herein, to detect deviations and recognize patterns of deviation for diagnostic purposes. Measured data, estimates, and residuals may be made available to medical staff on a display system, or over a website, accessible locally and/or remotely. Also made available in such a display are any detected deviations, recognized patterns, and resulting automatically generated suggested diagnoses. The computer may provide, either via its interfaces or via web browser or client server programs to other workstations, a user interface for annotating the medical record of the patient regarding the residuals, deviations, patterns and diagnoses. Diagnoses may be marked as "under investigation", "incorrect", "confirmed", or other statuses by medical personnel. The user may also mark certain observations of data that have been flagged by the computer as a deviation or the like, as in fact normal, non-deviating data. In response, an adaptation module of the computer may use the actual data to modify the model which flagged the data as anomalous, whereafter any further such data would not be detected as anomalous by the model.

The process of adapting a model comprises adding a new observation or set of observations, to a set of reference data from which the original kernel-based model was "trained". In the simplest embodiment, all reference data is used as the model exemplars, and therefore adapting a model means adding the new observation(s) to the exemplar set of the model. If a training method has been used to downsample the reference observations to a subset stored as "representative" of system dynamics, then the new observations are added to the original reference dataset, and the downsampling technique is applied to derive a new representative exemplar set, which should then include representation of the new observations. It is also possible to merely add the new observations to a downsampled set of exemplars, without rerunning the downsampling technique. Furthermore, in that case, it may be useful to remove some exemplars from the model so that they are effectively replaced by the new observations, and the model size is kept at a manageable size. The criteria for which old exemplars to remove can include clustering and similarity determinations which compare the new observations to the old and replace those most like the new observations.

In the context of home or field monitoring of a person's health status, a wearable or carryable computing device equivalent to the likes of a PDA or cell phone, records data from a plurality of sensors attached to the person, either over direct wire connections or over extreme local wireless communication such as bluetooth. The data is retained in the computing device for downloading to a base station. If the computing device is also a wireless communication device such as a cell phone, it may upload the data over the communications network to a remote computer for analysis. Otherwise, the computing device can download the data to a base station over Bluetooth when in range, or via a wired cradle for linking the device to a computer. The uploaded or downloaded data is then periodically processed as it is made available, using the model-based monitoring approach of the present invention. If data is uploaded to a remote computer, that remote computer (or a computer networked with it) has access to the models required to process the data. If the data is downloaded to a local personal computer, e.g., a home computer, the model data can reside there for local analysis, or that computer can be configured to upload the data to a remote computer, e.g., over an internet connection, where the remote computer has the models required to process the data. Results of the processing, such as estimates, residuals, detected deviations/alerts, health/severity indicators and automated diagnoses, can be made available from the remote computers in the form of a website, or can be transmitted to an intended recipient. In any event, the model(s) used to process the data can be generic models comprised of exemplar observations from other humans, or can be a personalized model comprised of prior observations of the person being monitored.

It will be appreciated by those skilled in the art, that modifications to the foregoing preferred embodiments may be made in various aspects. Other variations clearly would also work, and are within the scope and spirit of the invention. The present invention is set forth with particularity in the appended claims. It is deemed that the spirit and scope of that invention encompasses such modifications and alterations to the preferred embodiment as would be apparent to one of ordinary skill in the art and familiar with the teachings of the present application.

What is claimed is:

1. A computer-automated monitoring system for early detection of incipient health problems in a monitored patient, comprising:
   a computer-accessible memory for storing a set of exemplary data observations of multiple vital signs obtained from said monitored patient comprising a personalized model of said patient;
   a data feed for receiving new data observations of said multiple vital signs from said monitored patient;
   a computer configured by a kernel-based modeling software module to generate an estimate of the value of at least one of said multiple vital signs, as a weighted combination of a subset of said exemplary data observations where said weights are determined from a kernel function comparison of said subset of exemplary data observations and a said received observation;
   said computer being further configured by a localization software module to select said subset of exemplary data observations based on at least some of the vital signs in said received observation;
   said computer being further configured by a residual analysis software module to compare said estimate to the corresponding measured value of the at least one of said multiple vital signs in said received data observation to generate a residual; and
   said computer being further configured by an alerting module having a rules system configurable to provide a test, wherein the test applies rules to said generated residual of each of a plurality of said multiple vital signs in combination to selectively trigger an alert, the alert being triggered based upon results of the test, and present said alert in a web based interface usable by a medical practitioner for monitoring said patient for incipient health problems.

2. A system according to claim 1, wherein said kernel-based modeling software module implements a similarity-based model.

3. A computer automated monitoring system according to claim 1, wherein said test of a said generated residual of each of a plurality of said multiple vital signs selected from the set of: said residual exceeds a threshold: said residual exceeds said threshold for a preselected number of data observations in a preselected window: said residual exceeds a running statistic of a time series of said residuals: and a sequential probability ratio test.

4. A computer automated monitoring system according to claim 3, wherein said multiple vital signs includes heart rate.

5. A computer automated monitoring system according to claim 3, wherein said multiple vital signs includes respiration rate.

6. A computer automated monitoring system according to claim 3, wherein said multiple vital signs includes heart rate variability.

7. A computer automated monitoring system according to claim 3, wherein said multiple vital signs includes a measure of a time lag between a QRS event and a subsequent blood pressure event.

8. A computer automated monitoring system according to claim 3, wherein said multiple vital signs includes a measure of a time lag between a respiratory activity and resulting oxygenation changes in the blood.

9. A computer automated monitoring system according to claim 3, wherein said multiple vital signs includes a measure of breathing depth.

10. A computer automated monitoring system according to claim 3, wherein said multiple vital signs includes a measure of activity.

11. A computer automated monitoring system according to claim 3, wherein said multiple vital signs includes a measure of the difference in temperature between the ambient air and the skin.

12. A computer automated monitoring system according to claim 3, wherein said multiple vital signs includes a measure of blood pressure.

13. A computer automated monitoring system according to claim 1, wherein said computer is further configured by an adaptation module disposed to add a received data observation to said set of exemplary data observations comprising said personalized model upon selection by a clinical user of an option to adapt said model responsive to an alert.

* * * * *